US008822437B2

(12) United States Patent
Ifuku et al.

(10) Patent No.: US 8,822,437 B2
(45) Date of Patent: Sep. 2, 2014

(54) CEREBRAL NERVE CELL NEOGENESIS AGENT (75) Inventors: Masataka Ifuku, Fukuoka (JP); Takehiko Fujino, Fukuoka (JP); Shirou Mawatari, Fukuoka (JP); Masaaki Sugiyama, Takatsuki (JP); Yoshirou Kodama, Takatsuki (JP); Hidetaka Fuchu, Takatsuki (JP); Keita Yunoki, Fukuoka (JP)

(73) Assignee: Marudai Food Co., Ltd., Osaka (JP)

( * ) Notice: Subject to any disclaimer, the term of this patent is extended or adjusted under 35 U.S.C. 154(b) by 0 days.

(21) Appl. No.: 13/520,899

(22) PCT Filed: Jan. 6, 2011

(86) PCT No.: PCT/JP2011/050130
§ 371 (c)(1),
(2), (4) Date: Jul. 6, 2012

(87) PCT Pub. No.: WO2011/083827
PCT Pub. Date: Jul. 14, 2011

(65) Prior Publication Data
US 2012/0283223 A1  Nov. 8, 2012

(30) Foreign Application Priority Data
Jan. 6, 2010  (JP) .................................. 2010-001337

(51) Int. Cl.
*A61K 31/685*  (2006.01)
*C07F 9/10*  (2006.01)
*A61P 25/28*  (2006.01)
*A61P 25/18*  (2006.01)
*A61P 25/24*  (2006.01)
*A61P 25/00*  (2006.01)

(52) U.S. Cl.
USPC ............................................ 514/114; 554/80

(58) Field of Classification Search
CPC ..... A61K 31/685; A61K 38/12; A61K 35/57; A25L 1/30
See application file for complete search history.

(56) References Cited

U.S. PATENT DOCUMENTS 4,687,783 A     8/1987  Hörrmann
5,759,585 A  *  6/1998  Forgeot ......................... 424/570
2004/0131644 A1 *  7/2004  Kang et al. .................. 424/283.1
2010/0105635 A1    4/2010  Miyazawa et al.
2011/0160471 A1    6/2011  Nadachi et al.

FOREIGN PATENT DOCUMENTS

| EP | 2 127 536 | 12/2009 | | |
|---|---|---|---|---|
| EP | 2 620 154 | 7/2013 | | |
| JP | 10-505614 | 6/1998 | | |
| JP | 2001-31572 | 2/2001 | | |
| JP | 2003-3190 | 1/2003 | | |
| JP | 2003-12520 | 1/2003 | | |
| JP | 2004-26803 | 1/2004 | | |
| JP | 2004026803 | * | 1/2004 | ........... A61K 31/685 |
| JP | 2007-262024 | 10/2007 | | |
| WO | 2008/093709 | 8/2008 | | |
| WO | 2008/146942 | 12/2008 | | |
| WO | 2009/154309 | 12/2009 | | |

OTHER PUBLICATIONS

Han et al. in Journal of Neurochemistry (2001) 77, 1167-1180.*
Norton et al. in Journal of Neurochemistry (1996) 13, 213-222.*
International Search Report issued Mar. 15, 2011 in International (PCT) Application No. PCT/JP2011/050130.
Teruo Miyazawa, "*Functional foods for supporting smart again in human*", Journal of Japanese Society for Integrative Medicine, 2008, vol. 1, No. 1, pp. 84-90, with English abstract.
Juan M. Encinas et al., "*Fluoxetine targets early progenitor cells in the adult brain*", Proceedings of the National Academy of Sciences, 2006, vol. 103, No. 21, pp. 8233-8238.
Supplementary European Search Report issued May 16, 2013 in corresponding European Patent Application No. 11731825.3.
P. Brites et al., "Functions and biosynthesis of plasmalogens in health and disease", Biochimica et Biophysica Acta, vol. 1636, No. 2-3, pp. 219-231, Mar. 22, 2004.
C. Tessier et al., "Pe Plasmalogen in Erythrocyte Membranes From Patients With Schizophrenia.: A Comparison With Healthy Subjects", Schizophrenia Research, vol. 102, No. 1-3, Jun. 2008, p. 209.
Examination Report issued Jan. 24, 2014 in corresponding European Patent Application No. 11731825.3.

* cited by examiner

*Primary Examiner* — Dennis Heyer
(74) *Attorney, Agent, or Firm* — Wenderoth, Lind & Ponack, L.L.P.

(57) ABSTRACT

An objective of the present invention is to provide a new substance having a cerebral nerve cell neogenesis effect. Another objective is to provide a cerebral nerve cell neogenesis agent that is effective in treating and/or preventing neurological disorders utilizing the substance. With the present invention, a cerebral nerve cell neogenesis agent containing a plasmalogen as an active ingredient is provided. In particular, a preferable cerebral nerve cell neogenesis agent contains, as an active ingredient, a biological tissue (preferably, an avian tissue) extracted plasmalogen mainly including an ethanolamine plasmalogen and a choline plasmalogen.

5 Claims, 2 Drawing Sheets

Fig. 1

Fig. 2

CEREBRAL NERVE CELL NEOGENESIS AGENT

TECHNICAL FIELD

The present invention relates to a cerebral nerve cell neogenesis agent (i.e., an agent for neogenesis of a cerebral nerve cell) containing, as an active ingredient, a plasmalogen; and more specifically, relates to a cerebral nerve cell neogenesis agent, containing, as an active ingredient, a plasmalogen extracted from a biological tissue.

BACKGROUND ART

In recent years, particularly in advanced nations, the number of people suffered from neurological and psychiatric disorders has increased. Causes of these disorders are thought to be rapidly aging society and/or various stresses. More specifically, it is estimated that the number of people with dementia such as Alzheimer's disease has increased due to an age-associated decline in cerebral functions combined with some other factors. Furthermore, it is thought that the number of people with schizophrenia or depression has increased due to various stresses that exist in modern society.

Hitherto, it has been considered that cerebral nerve cells largely contribute to cerebral functions. For example, in the above described neurological disorders, although their respective causes are different, various changes including sclerosis, atrophy, death, or reduction of cerebral nerve cells can be observed therein. Therefore, there are expectations for a possible treatment to prevent progression of neurological disorders by hindering such changes in the cerebral nerve cells. For example, Patent Literature 1 discloses that dictyosterol has an effect of enabling survival and sustention of nerve cells when they are damaged and enhancing formation and outgrowth of neurites; and thereby suggests that dictyosterol may be used for treating neurological disorders. Furthermore, Patent Literature 2 suggests that a plasmalogen (phosphatidylethanolamine) has a nerve cell death inhibiting effect.

In addition, there is an expectation that a better therapeutic effect can be obtained by inducing neogenesis of cerebral nerve cells rather than stopping changes in cerebral nerve cells as described above. In recent years, it has been revealed that neogenesis of nerve cells are occurring even in adults of many mammals including humans. In particular, neogenesis of nerve cells in the hippocampal dentate gyrus is thought to have a large contribution in the development of regenerative therapy for neurodegenerative disorders such as Alzheimer's disease and Parkinson's disease. For example, it is reported that fluoxetine which is a therapeutic agent for depression increases the number of cerebral nerve cells in 3 to 4 weeks (Non-Patent Literature 1), and the increase is inferred to contribute to an antidepressive effect of the therapeutic agent.

However, substances having an effect of inducing neogenesis in cerebral nerve cells are almost unknown, and thereby there has been a desire for a new substance capable of inducing neogenesis in cerebral nerve cells safely and efficiently.

CITATION LIST

Patent Literature

PTL 1: Japanese Unexamined Patent Publication No. 2001-31572
PTL 2: Japanese Unexamined Patent Publication No. 2004-26803

Non-Patent Literature

NPL 1: Proceedings of the National Academy of Sciences 2006 103: 8233-8238

SUMMARY OF INVENTION

Technical Problem

An objective of the present invention is to provide a new substance having a cerebral nerve cell neogenesis effect.

Solution to Problem

The present inventors have discovered surprisingly that a plasmalogen has a cerebral nerve cell neogenesis effect, and have accomplished the present invention after further improvements. It should be noted that, although a person skilled in the art will understand naturally, those described as "mass %" may be substituted with "weight %".

That is, the present invention includes, for example, themes described in the following items.

Item 1.
A cerebral nerve cell neogenesis agent containing a plasmalogen as an active ingredient.

Item 2-1.
The cerebral nerve cell neogenesis agent according to claim 1, containing, as an active ingredient, a plasmalogen extracted from a biological tissue.

Item 2-2.
The cerebral nerve cell neogenesis agent according to item 1, containing, as an active ingredient, a plasmalogen-containing biological tissue extract.

Item 3-1.
The cerebral nerve cell neogenesis agent according to claim 2-1, containing, as an active ingredient, a plasmalogen extracted from an avian tissue.

Item 3-2.
The cerebral nerve cell neogenesis agent according to item 2-2, containing, as an active ingredient, a plasmalogen-containing avian tissue extract.

Item 4.
The cerebral nerve cell neogenesis agent according to any one of items 1 to 3-2, wherein the plasmalogen includes an ethanolamine plasmalogen and a choline plasmalogen.

Item 5.
The cerebral nerve cell neogenesis agent according to item 4, wherein not less than 90 mass % of the plasmalogen is the ethanolamine plasmalogen and the choline plasmalogen.

Item 6.
The cerebral nerve cell neogenesis agent according to item 4 or 5, wherein the plasmalogen includes the ethanolamine plasmalogen and the choline plasmalogen, and a mass ratio of (ethanolamine plasmalogen:choline plasmalogen) is (1:5) to (1:0.01).

Item 7-1.
The cerebral nerve cell neogenesis agent according to any one of items 1 to 6, utilized for treating and/or for preventing a neurological disorder accompanied by sclerosis, atrophy, death, or reduction of cerebral nerve cells.

Item 7-2.
The cerebral nerve cell neogenesis agent according to item 7-1, wherein the neurological disorder accompanied by sclerosis, atrophy, death, or reduction of cerebral nerve cells is at least one type of neurological disorder selected from the group consisting of Alzheimer's disease, depression, schizophrenia, and dementia.

Item 8-1.

A composition containing a plasmalogen, and a pharmaceutically acceptable carrier or a food-hygienically acceptable carrier.

Item 8-2.

A composition containing a plasmalogen-containing avian tissue extract, and a pharmaceutically acceptable carrier or a food-hygienically acceptable carrier.

Item 9-1.

A cerebral nerve cell neogenesis method comprising a step of causing a subject to take in a plasmalogen at an effective dose.

Item 9-2.

A cerebral nerve cell neogenesis method comprising a step of causing a subject to take in a plasmalogen-containing avian tissue extract at an effective dose.

Item 9-3.

A cerebral nerve cell neogenesis method comprising a step of causing a subject to take in, at an effective dose, the cerebral nerve cell neogenesis agent according to any one of items 1 to 7.

Item 10.

The cerebral nerve cell neogenesis method according to any one of items 9-1 to 9-3, wherein the subject is a mammal including human.

Item 11-1.

The cerebral nerve cell neogenesis method according to any one of items 9-1 to 10, wherein the subject is a subject that has developed a neurological disorder accompanied by sclerosis, atrophy, death, or reduction of cerebral nerve cells.

Item 11-2.

The cerebral nerve cell neogenesis method according to item 11-1, wherein the neurological disorder accompanied by sclerosis, atrophy, death, or reduction of cerebral nerve cells is at least one type of neurological disorder selected from the group consisting of Alzheimer's disease, depression, schizophrenia, and dementia.

Item 12-1.

A plasmalogen for use in treating or preventing a neurological disorder accompanied by sclerosis, atrophy, death, or reduction of cerebral nerve cells.

Item 12-2.

A plasmalogen-containing avian tissue extract for use in treating or preventing a neurological disorder accompanied by sclerosis, atrophy, death, or reduction of cerebral nerve cells.

Item 12-3.

The cerebral nerve cell neogenesis agent according to any one of items 1 to 7, for use in treating or preventing a neurological disorder accompanied by sclerosis, atrophy, death, or reduction of cerebral nerve cells.

Item 12-4.

The composition according to item 8-1 or 8-2, for use in treating or preventing a neurological disorder accompanied by sclerosis, atrophy, death, or reduction of cerebral nerve cells.

Item 12-5.

The plasmalogen according to item 12-1, the plasmalogen-containing avian tissue extract according to item 12-2, the cerebral nerve cell neogenesis agent according to item 12-3, or the composition according to item 12-4, wherein the neurological disorder accompanied by sclerosis, atrophy, death, or reduction of cerebral nerve cells is at least one type of neurological disorder selected from the group consisting of Alzheimer's disease, depression, schizophrenia, and dementia.

Item 13-1.

Use of a plasmalogen in the manufacture of a medicament for the treatment of a neurological disorder accompanied by sclerosis, atrophy, death, or reduction of cerebral nerve cells.

Item 13-2.

Use of a plasmalogen-containing avian tissue extract in the manufacture of a medicament for the treatment of a neurological disorder accompanied by sclerosis, atrophy, death, or reduction of cerebral nerve cells.

Item 13-3.

The use according to item 13-1 or 13-2, wherein the plasmalogen includes an ethanolamine plasmalogen and a choline plasmalogen.

Item 13-4.

The use according to item 13-3, wherein not less than 90 mass % of the plasmalogen is the ethanolamine plasmalogen and the choline plasmalogen.

Item 13-5.

The use according to item 13-3 or 13-4, wherein the plasmalogen includes the ethanolamine plasmalogen and the choline plasmalogen, and a mass ratio of (ethanolamine plasmalogen:choline plasmalogen) is (1:5) to (1:0).

Item 13-6.

The use according to any one of items 13-1 to 13-5, wherein the neurological disorder accompanied by sclerosis, atrophy, death, or reduction of cerebral nerve cells is at least one type of neurological disorder selected from the group consisting of Alzheimer's disease, depression, schizophrenia, and dementia.

Advantageous Effects of Invention

With a cerebral nerve cell neogenesis agent of the present invention, which includes a plasmalogen as an active ingredient, cerebral nerve cells (in particular, cerebral nerve cells of the dentate gyrus) can be newly generated and can be increased. Therefore, with the cerebral nerve cell neogenesis agent, it is conceivable to treat various neurological disorders. In particular, it is conceivable that an excellent effect can be obtained in treating and/or preventing neurological disorders (e.g., Alzheimer's disease, depression, schizophrenia, and dementia) in which sclerosis, atrophy, death, or reduction etc., of cerebral nerve cells can be observed.

In addition, the cerebral nerve cell neogenesis agent of the present invention can induce neogenesis particularly in cerebral nerve cells of the dentate gyrus. The dentate gyrus is one region of the hippocampus that manages memory, and since it is thought to play an important role in inputting information to the hippocampus; it is conceivable that the cerebral nerve cell neogenesis agent of the present invention can have an advantageous effect in improving and treating memory disorders, or improving learning ability such as learning memory.

Plasmalogen is the active ingredient in the cerebral nerve cell neogenesis agent of the present invention. Plasmalogen is a component included in many biological tissues. Therefore, when a plasmalogen extracted from a biological tissue that is hitherto known as edible is used, there is almost no concern regarding side effects etc., of the agent, and it is thought that safety of the agent is extremely high.

DESCRIPTION OF EMBODIMENTS

In the following, further details of the present invention will be set forth.

The present invention relates to a cerebral nerve cell neogenesis agent including a plasmalogen as an active ingredient.

A plasmalogen normally refers to a glycerophospholipid having a long-chain alkenyl group at position 1 of a glycerol skeleton via a vinyl ether linkage. A general formula of plasmalogens is shown in the following.

In the formula, $R^1$ and $R^2$ each represents an aliphatic hydrocarbon group. $R^1$ is normally an aliphatic hydrocarbon group having a carbon number of 1 to 20, and includes, for example, dodecyl group, tetradecyl group, hexadecyl group, octadecyl group, icosanyl group, etc. $R^2$ is normally an aliphatic hydrocarbon group derived from an aliphatic acid residue, and includes, for example, octadecadienoyl group, octadecatrienoyl group, icosatetraenoyl group, icosapentaenoyl group, docosatetraenoyl group, docosapentaenoyl group, docosahexaenoyl group, and the like. Furthermore, in the formula, X represents a polar group. X is preferably —$CH_2CH_2NH_2$, —$CH_2CH_2N^+(CH_3)_3$, —$CH_2CH(NH_2)$COOH, or, X is preferably a group in which a compound (H—X) resulting from X binding to H is inositol or glycerol.

In particular, plasmalogens existing in nature are mainly ethanolamine plasmalogens in which X in the above described formula is an aminoethyl group (—$CH_2CH_2NH_2$) and choline plasmalogens in which X is a trimethyl aminoethyl group (—$CH_2CH_2N^+(CH_3)_3$). These two types are particularly preferable as the plasmalogens contained in the cerebral nerve cell neogenesis agent of the present invention. Thus, the cerebral nerve cell neogenesis agent of the present invention preferably contains, as the plasmalogen, an ethanolamine plasmalogen and/or a choline plasmalogen.

The plasmalogen used in the present invention is preferably extracted from a biological tissue. Here, a biological tissue is a tissue containing a plasmalogen in an organism. The organism used for extracting the plasmalogen includes, for example, animals and microorganisms. As the microorganisms, anaerobic bacteria are suitable, and, for example, bacteria in the family Acidaminococcaceae which are intestinal bacteria are particularly preferable. In the case with bacteria, "biological tissue" refers to the bacteria themselves. Suitable animals include birds, mammals, fishes, shellfishes, and the like. As the mammals, livestock are preferable from both aspects of stable supply and safety, and examples of the mammals include cow, pig, horse, sheep, goat, etc. In the case with mammals, tissues containing a plasmalogen include skin, brain, intestines, heart, genitals, and the like; and the plasmalogen can be extracted from these tissues. Furthermore, the birds include chicken, domestic duck, quail, duck, pheasant, ostrich, turkey, and the like. When aspects such as cost and ease of acquiring, and resistance against putting them in his/her mouth are taken into consideration, chicken is particularly preferable since it is conventionally used as food and is widely circulated in the market. Furthermore, there is no particular limitation in the avian tissue that is to be used, and, for example, bird meat (in particular, bird breast meat), bird skin, internal organs of birds, etc., are suitably used. It should be noted that two or more types of different tissues from one or more species of organisms may be used in combination.

For the present invention, as the plasmalogen extracted from a biological tissue, usage of plasmalogen extracted from an avian tissue is particularly preferable. Above all, birds (poultry) that have been conventionally used as food are proven to be safe and are easy for stable supplying, and thereby are preferable. Chicken is most preferable.

There is no particular limitation in the method for extracting the plasmalogen from a biological tissue as long as the plasmalogen can be extracted (and can be purified if necessary). A hitherto known plasmalogen extraction method may be selected as appropriate. For example, an extraction product that has been extracted using water, an organic solvent, or a hydrous organic solvent can be used as a plasmalogen-containing biological tissue extract. Additionally, for example, extraction and purification are preferable conducted on the extract as described in detail in the following. The method for extraction and purification is a method including the following steps of (1) to (3).

(1) A step of removing neutral lipids and sphingolipids from a biological tissue extract.

(2) A step of hydrolyzing the extract obtained through step (1).

(3) A step of removing diacyl-type glycerophospholipid degradation products from the extract obtained through step (2).

This method for extraction and purification is also preferable since diacyl-type glycerophospholipids can be degraded/removed and thereby the purity of the plasmalogen can be further increased. The extract obtained in the above described manner can be favorably used as a plasmalogen-containing biological tissue extract. It should be noted that, hereinafter, "a plasmalogen extracted from a biological tissue" may be described as "a biological-tissue extracted plasmalogen." In, addition, for example, "a plasmalogen extracted from an avian tissue" may be described as "an avian-tissue extracted plasmalogen."

The extraction is preferably conducted through an extraction using water or an organic solvent (e.g., at least one organic solvent selected from the group consisting of methanol, ethanol, propanol, butanol, isopropanol, acetone, and hexane), or a hydrous organic solvent. The water content (v/v %) of the hydrous organic solvent is not particularly limited, and may be, for example, 10 to 90%. In particular, an extraction using ethanol or hydrous ethanol is preferable. Furthermore, the avian tissue on which the extraction is to be conducted may be raw, or may be pre-processed in some manner. For example, the avian tissue may be one that is dried and/or deoiled in advance.

Although there is no particular limitation in extraction processing conditions, immersion methods such as cold extraction, warm extraction, etc., and percolation methods, and the like may be used. One suitable example is a method of adding ethanol to chicken breast meat, and keeping the mixture still or stirring the mixture at 30° C. or higher for 60 minutes or more, preferably at 40° C. or higher for 180 minutes or more. For example, this can be done by using, with respect to 1 kg of dried chicken breast meat, for example, 1 to 10 L of ethanol, preferably 1 to 6 L, and further preferably 2 to 4 L.

An obtained organic solvent extraction solution is preferably condensed and dried to be formed into a solid, and then subjected through a hydrolysis processing step. The condensing and drying for forming a solid can be conducted in accordance with a method known in the art, and, for example, can be conducted using an evaporator. An organic-solvent extract (organic solvent extraction dry-solid) is obtained in the manner described above. Lipids such as plasmalogens and the like are contained in the organic solvent extraction dry-solid in a condensed manner.

Furthermore, preferably, the organic solvent extraction dry-solid is, for example, centrifuged in acetone to recover a precipitate, and then centrifuged in a hexane/acetone mixed solvent to recover a liquid layer. Although a restrictive interpretation is not desired, neutral lipids can be removed by recovering a precipitate after centrifugation in acetone, and sphingolipids can be removed by recovering a liquid layer after centrifugation in a hexane/acetone mixed solvent.

A phospholipid condensed dry-solid can be obtained by condensing and drying the obtained liquid layer to form a solid. Plasmalogens can be favorably condensed by subjecting the phospholipid condensed dry-solid through a hydrolysis processing step to hydrolyze diacyl-type phospholipids.

Such hydrolysis process includes, for example, treatment with phospholipase A1 (PLA1). PLA1 specifically hydrolyzes a linkage part between a sn-1 aliphatic acid and a glycerin skeleton in a diacyl-type phospholipid. In contrast, sn-1 in plasmalogens is an ether linkage, and thereby is not subjected to an action of PLA1. Therefore, treatment with PLA1 degrades diacyl-type glycerophospholipids but plasmalogens will not be degraded. Treatment using PLA1 degrades diacyl-type glycerophospholipids into free aliphatic acids and lysophospholipids. As a result of converting diacyl-type glycerophospholipids that coexist with plasmalogens into lyso-form using PLA1, and removing free aliphatic acids and lysophospholipids, plasmalogens can be purified.

With regard to PLA1, there is no particular limitation in its origin etc., as long as the above described advantageous effect can be obtained. Examples thereof include PLA1 derived from *Aspergillus oryzae*. Furthermore, such PLA1 can be purchased from, for example, Mitsubishi-Kagaku Foods Corporation etc. In addition, a usage amount of it can be set as appropriate in accordance with an amount of the organic solvent extraction dry-solid that is to be used. Preferably, 0.2 to 200 unit/(1 mg of the organic solvent extraction dry-solid) is used; and further preferably, 2 to 200 unit/(1 mg of the organic solvent extraction dry-solid) is used. It should be noted that 1 unit refers to an amount (1 µmol/min) for transforming 1 µmol of a substrate (diacyl-type glycerophospholipid) in 1 minute.

Furthermore, a buffer that is to be used can be selected as appropriate in accordance with the used PLA1. For example, a 0.1 M citric acid-HCl buffer (pH4.5) can be used. In such a case, the buffer can be added to dissolve the organic solvent extraction dry-solid, and then PLA1 can be added therein. Furthermore, the amount of the buffer that is to be used is not particularly limited as long as it allows enzyme reaction to proceed; and, preferably, it is 1 to 30 mL for 1 g of the organic solvent extraction dry-solid, and further preferably about 5 to 15 mL.

Although conditions for the reaction can also be set as appropriate, preferably, the reaction is conducted at 50° C. for 1 to 2 hours while stirring.

It should be noted that an inactivation treatment may be conducted on the enzyme after the hydrolysis reaction. Preferably, the treatment is conducted by increasing the temperature to about 70° C. after the hydrolysis reaction.

In the manner described above, a processed liquid (hydrolysis processed liquid) in which diacyl-type glycerophospholipids are degraded can be obtained. By adding thereto, for example, hexane at a volume 2 to 3 times of that of the hydrolysis processed liquid, centrifuging the mixture, and recovering a liquid layer (hexane layer); the enzyme buffer and enzyme protein can be removed (the enzyme buffer and enzyme protein are dissolved in the water layer and are not contained in the hexane layer).

In addition, since plasmalogens are soluble to hexane but poorly soluble to acetone, lysophospholipids can be removed and plasmalogens can be condensed, through segregating using hexane and acetone, and water as appropriate in combination, and then further segregating the solution with water or a solution (aqueous solution). (Neutral lipids other than phospholipids can be removed with acetone, and plasmalogens and lysophospholipids can be separated through segregating of the aqueous solution).

For example, the biological-tissue extracted plasmalogen extracted and purified as described above can be favorably used as an active ingredient of the cerebral nerve cell neogenesis agent of the present invention. In addition, a composition (i.e., plasmalogen-containing biological tissue extract) extracted from a biological tissue containing a plasmalogen can also be used as an active ingredient of the cerebral nerve cell neogenesis agent of the present invention.

The biological-tissue extracted plasmalogen mainly includes an ethanolamine plasmalogen and/or a choline plasmalogen. Although not particularly limited, a mass ratio (ethanolamine plasmalogen:choline plasmalogen) in the biological-tissue extracted plasmalogen is preferably (1:5) to (1:0), more preferably (1:5) to (1:0.01), further preferably (1:5) to (5:1), still further preferably (1:3) to (3:1), even further preferably (1:2) to (2:1), and even still further preferably (1:1.5) to (1.5:1).

It should be noted that, it is known that plasmalogens that exist mainly in the brain are ethanolamine plasmalogens, and choline plasmalogens almost do not exist therein. Thus, the fact that the biological-tissue extracted plasmalogen containing a choline plasmalogen can be favorably used in the cerebral nerve cell neogenesis is completely unexpected.

In addition, although not particularly limited, the contained amount of the ethanolamine plasmalogen and the choline plasmalogen in the biological-tissue extracted plasmalogen used in the present invention is preferably not less than 50 mass %, more preferably not less than 60 mass %, further preferably not less than 70 mass %, still further preferably not less than 80 mass %, and particularly preferably not less than 90 mass %.

The mass ratio and contained amount of the ethanolamine plasmalogen and choline plasmalogen can be obtained, for example, by analyzing the biological-tissue extracted plasmalogen using high performance liquid chromatography (HPLC). Specifically, the mass ratio can be obtained with the HPLC by obtaining a chromatogram using an evaporative light scattering detector (ELSD) (i.e., the mass ratio can be obtained with HPLC-ELSD), and obtaining an area ratio of respective peaks representing the ethanolamine plasmalogen and the choline plasmalogen in the chromatogram. Furthermore, the contained amount can be obtained by calculating what % of a peak area of the entire chromatogram is the peak area representing the ethanolamine plasmalogen and the choline plasmalogen. This is because, with ELSD, substances having similar structures show a similar area response. It should be noted that, since a choline type is electrically neutral, whereas ethanolamine is weakly acidic due to the negative charge of phosphate, it is preferable to conduct the analysis after, for example, charging acidic lipids using acetic acid and triethylamine as solvents. This is because a more similar area response can be obtained with the charging.

In addition, it is also possible to obtain the mass ratio and contained amount by, for example, quantifying the amount of the ethanolamine plasmalogen and the choline plasmalogen through analysis using LC-MS and the like.

The cerebral nerve cell neogenesis agent of the present invention can be favorably used in the pharmaceutical field and food field. The agent includes the plasmalogen (preferably, biological-tissue extracted plasmalogen). As described in detail in the following, the agent may consist only of the plasmalogen, or may be a composition containing the plasmalogen and other components (various bases, carriers, additives, etc.). The plasmalogen-containing biological tissue extract itself is also included in the composition. Thus, the plasmalogen-containing biological tissue extract (and one obtained by blending therein other components if necessary) can also be used as the agent.

When the cerebral nerve cell neogenesis agent of the present invention is used in the pharmaceutical field, the agent (hereinafter, may be described as "a pharmaceutical agent according to the present invention") may consist only of the plasmalogen, or may be a pharmaceutical composition including other components blended therein. For example, for the pharmaceutical agent according to the present invention, if necessary, it is possible to blend, together with the plasmalogen which is the active ingredient, pharmaceutically acceptable bases, carriers, additives (e.g., for excipients, binders, disintegrants, lubricants, solvents, sweetening agents, coloring agents, corrigents, odor-masking agents, surfactants, moisturizers, preservatives, pH adjusters, thickening agents, etc.), and the like. Such base materials, carriers, additives, etc., are described, for example, in Pharmaceutical Additive Dictionary 2000 (Yakuji Nippo Ltd.,); and, for example, those described therein can be used. In addition, there is no particular limitation in the preparation form, and a hitherto known method can be used for mixing the active ingredient and other components, and preparing the preparation in forms such as, tablets, coated tablets, powder, granule, subtle granule, capsules, pills, liquid agents, suspensions, emulsions, jellies, chewable agents, soft tablets, etc.

For example, a tabletting method can be used for producing a tablet. Either of a direct tabletting method of directly tabletting mixed raw materials, or a granule tabletting method of tabletting granulated raw materials that have been mixed may be used.

A blend amount of the plasmalogen in the pharmaceutical agent according to the present invention is not particularly limited as long as a cerebral nerve cell neogenesis action is exerted, and can be set as appropriate in accordance with a preferable per day intake amount of the plasmalogen. Preferably, it is 0.0005 to 100 mass %, more preferably, 0.005 to 90 mass %, and further preferably 0.05 to 80 mass %.

A subject that is to be administered with the pharmaceutical agent according to the present invention is not limited, and preferably is a patient who has developed, for example, a neurological disorder in which a change such as sclerosis, atrophy, death, or reduction of cerebral nerve cells is observed. Examples of such neurological disorder include dementia (Alzheimer's disease, Parkinson's disease, etc.), schizophrenia, depression, etc. Furthermore, there is not particular limitation in the severity of illness of the patient who is to be administered with the agent, and the agent can be favorably administered to any patient such as early stage patients, intermediate stage patients, and later stage patients. In addition, it is also possible to preventatively use the agent for people having a high possibility of developing the above described neurological disorders, such as elderly people etc.

Furthermore, the subject to be administered with the pharmaceutical agent according to the present invention is not limited to humans but also includes non-human mammals. Examples thereof include mammals showing symptoms similar to the above described symptoms for humans, and in particular, mammals reared as pets and livestock are preferable. Specifically, examples thereof include dogs, cats, monkeys, cows, horses, sheep, goats, pigs, rabbits, mice, rats, camels, llamas, etc. Similar to the case with humans, the pharmaceutical agent according to the present invention can be used preventatively also for mammals.

There is no particular limitation in the time for administering the cerebral nerve cell neogenesis agent of the present invention. The time for administration can be selected as appropriate by taking into consideration, for example, preparation form, age of an administration subject, the severity of the symptom of the administration subject, etc. Furthermore, although there is no particular limitation in the administration mode, oral administration is particularly suitable.

An administration dose of the cerebral nerve cell neogenesis agent of the present invention can be selected as appropriate in accordance with the age of the administration subject, the severity of the symptom of the administration subject, other conditions, etc. Ordinarily, a per day amount of the plasmalogen in the agent for an adult is preferably set in a range of 1 to 1000 mg, and more preferably 10 to 100 mg. It should be noted that the administration can be conducted once or separately in multiple times (preferably, 2 to 3 times) per day. The administration dose can be set as appropriate also for the mammals, using the case with humans as a reference.

When using the cerebral nerve cell neogenesis agent of the present invention as a food additive for cerebral nerve cell neogenesis, such agent (hereinafter, may be described as "a food additive according to the present invention") may consist only of the plasmalogen, or maybe a food additive composition having appropriately blended therein the plasmalogen, food-hygienically acceptable bases, carriers, additives, and other components and materials that can be used as food additives. Furthermore, examples of forms of the food additive include, but not limited to, liquid, powder, flake forms, granules, and paste forms. Specific examples thereof include seasonings (soy sauce, Worcestershire sauce, ketchup, dressing, etc.), flakes (Furikake), Yakiniku sauces, spices, roux pastes (curry roux paste etc.), and the like. These food additives can be appropriately prepared in accordance with hitherto known methods. The blend amount of the plasmalogen in the food additive according to the present invention is not particularly limited as long as the cerebral nerve cell neogenesis action is exerted, and is preferably 0.0005 to 100 mass %, more preferably 0.005 to 90 mass %, and further preferably 0.05 to 80 mass %.

The food additive according to the present invention is ingested through eating of a food product having added thereto the food additive. It should be noted that the adding may be conducted while the food is being cooked or produced, or may be conducted immediately before or while eating a cooked food product. When the food additive is orally ingested as described above, the cerebral nerve cell neogenesis effect is exerted. With regard to the food additive according to the present invention, although there are no particular limitations in the intake amount, intake subject, measuring of the contained amount of the plasmalogen, etc.; for example, those similar to the above described pharmaceutical agent according to the present invention are preferable.

When the cerebral nerve cell neogenesis agent of the present invention is used as food or beverage for cerebral nerve cell neogenesis, such agent (hereinafter, may be described as "food or beverage according to the present invention") is obtained by appropriately blending the plasmalogen, food-hygienically acceptable bases, carriers, additives, and other components and materials that can be used as food or beverage. Examples thereof include food compositions such as plasmalogen containing processed food for cerebral nerve cell neogenesis or for improving or preventing symptoms of neurological disorders, plasmalogen containing drinks, plasmalogen containing health food (nutritional performance food, Food for Specified Health Uses, etc.), plasmalogen containing supplements, and plasmalogen containing food products for patients (hospital diets, sick diets, nursing-care food, or the like). When the plasmalogen blended in the agent is the biological-tissue extracted plasmalogen extracted from livestock or poultry (e.g., cow, pig, chicken, etc.), for example, the agent is preferably, but not particularly limited to, plasmalogen mixed processed flesh food such as hamburger, meatball, Vienna sausage, chicken Soboro, chicken skin chips, etc., plasmalogen mixed health food (nutritional performance food, Food for Specified Health Uses, etc.), plasmalogen mixed supplements, and plasmalogen mixed food products for patients, and the like containing processed flesh food. In addition, it is also possible to, for example, turn the plasmalogen into a powder, and have it included in various food or beverages such as beverages (juice etc.), confectioneries (e.g., gum, chocolate, candy, biscuit, cookie, Okaki, Senbei, pudding, Chinese-style almond jelly, etc.), bread, soup (including powdered soup etc.), processed food, etc.

When the food or beverage according to the present invention is prepared as a health food (nutritional performance food, Food for Specified Health Uses, etc.) or a supplement; to make sustained ingestion easier, the food or beverage is preferably prepared in form such as, for example, granules, capsules, tablets (including chewable agents etc.), drinks (drinkable preparation), and the like. Among those, from the standpoint of easy ingestion, forms such as capsules, tablets, and pills are preferable, but not particularly limited thereto. The cerebral nerve cell neogenesis agent made into the food or beverage according to the present invention in a form such as a granule, a capsule, a tablet, etc., can be appropriately prepared in accordance with a hitherto known method using pharmaceutically and/or food-hygienically acceptable carriers and the like. Furthermore, preparing other forms may also be conducted in accordance with hitherto known methods.

The blend amount of the plasmalogen in the food or beverage according to the present invention is not particularly limited as long as the cerebral nerve cell neogenesis action can be exerted, and is preferably 0.0005 to 100 mass %, more preferably 0.005 to 90 mass %, and further preferably 0.05 to 80 mass %.

The food or beverage according to the present invention can be favorably used for improving or preventing symptoms of neurological disorders. Although there are no particular limitations in the intake amount, intake subject, measuring of the contained amount of the plasmalogen, etc.; for example, those similar to the above described pharmaceutical agent according to the present invention are preferable.

It should be noted that a hospital diet is a meal provided to those admitted to a hospital, a sick diet is a meal for the sick, and nursing-care food is a meal for people under care. The food or beverage according to the present invention can be favorably used particularly as hospital diets, sick diets, or nursing-care food, for patients who are admitted to hospitals due to neurological disorders or who are recuperating therefrom at home, or for patients receiving nursing care. Furthermore, it is also possible for people having a high possibility of developing neurological disorders, such as elderly people etc., to preventatively ingest the food or beverage.

The present invention also provides a prevention method, an improving method, and a therapeutic method for neurological disorders; and features thereof include oral administration or ingestion of the cerebral nerve cell neogenesis agent of the present invention by a neurological disorder patient, and a person, a mammal, or the like having a high possibility of developing a neurological disorder. Specifically, the methods are implemented through administration or ingestion of the above described cerebral nerve cell neogenesis agent of the present invention. It should be noted that various conditions of the methods, such as the subject, administration route, or intake amount, etc., are identical to those described above.

EXAMPLES

The present invention will be set forth specifically in the following; however, the present invention is not limited to the following Examples.

Preparation Example 1

Production of Biological-Tissue Extracted Plasmalogen Containing Fraction

Chicken breast meat, which is an avian tissue, was collected in accordance with a hitherto known method, chopped into minced meat having a size of about 8 mm, heated for microbiological control, and then chilled-frozen and stored. Then, lyophilization was performed thereon using a hitherto known method, and the lyophilized product was grinder-processed to be ground. The dried breast meat powder was hermetically stored together with a deoxidant, until it was used for extraction.
<Organic Solvent Extraction Process>
Step (1)

4 L of ethanol was added to 1 kg of the dried breast meat powder obtained as described above, and the solution was stirred for 12 hours at 40° C. and left still. Then, an extraction solution was separated from solid matter. 2.5 L of ethanol was added to the solid matter and the extraction was performed again as previously described. The obtained extraction solutions were combined and filtered using a filter paper, and dried under reduced pressure to obtain a condensed extraction dry-solid.
Step (2)

8 mL of water was added to the above described extraction dry-solid and mixed. The mixture was centrifuged, and an upper layer of the mixture was removed. 200 mL of acetone was added to an obtained precipitate, and the mixture was stirred and centrifuged at 4° C. to remove an acetone layer therefrom. Then, 100 mL of acetone was added to an obtained precipitate, and the mixture was stirred and centrifuged to recover a precipitate. Next, 100 mL of a hexane/acetone (7:3) mixed solvent was added to an obtained precipitate, and the mixture was stirred and centrifuged to recover 20 g of a liquid layer (plasmalogen containing fraction). The liquid layer was immediately condensed and dried to form a solid using a rotating evaporator. It should be noted that the centrifugations were conducted at 3000 rpm for 10 minutes, that using acetone by itself and the hexane/acetone mixed solvent were performed at 4° C., and others were performed at 15° C.
Step (3)

20 g of the plasmalogen containing fraction obtained as described above was dispersed in 400 mL of a phospholipase A1 (Mitsubishi-Kagaku Foods Corporation) solution (10 mg/mL; 0.1M citric acid-HCl buffer), and the mixture was stirred for 2 hours at 50° C. under nitrogen gas. Then, the mixture was cooled, and hexane was added thereto at a volume 2 times of the mixture. The mixture was stirred and segregated twice, and an upper layer was recovered therefrom to be condensed and dried to form a solid. Next, 60 mL of acetone was added to the dry-solid, and an operation of stirring, centrifuging, and precipitate-recovering was repeatedly performed on the mixture twice. Then, 60 mL of hexane/acetone (7:3) was added to the precipitate, and the mixture was stirred and centrifuged to recover a liquid layer (highly pure plasmalogen containing fraction). 198 mL of hexane and 222 mL of acetone were added to the liquid layer (i.e., the total was hexane/acetone (1:1)), and the mixture was transferred to a separatory funnel, and 72 mL of water was added thereto, and stirring and segregating were performed. A lower layer (acetone layer) was removed, 192 mL of acetone/water (5:3) was added to an upper layer (hexane layer), and stirring and segregating were performed. An upper layer (hexane layer) was recovered, and immediately dried under reduced pressure to obtain a chicken breast meat derived highly pure plasmalogen containing substance.

<Examination of Purity of Chicken Breast Meat Derived Highly Pure Plasmalogen Containing Substance>

The chicken breast meat derived highly pure plasmalogen containing substance obtained as described above was analyzed using an HPLC with the following conditions to obtain a chromatogram.

[HPLC Analysis Condition]
Instrument; Shimadzu LC-10AD
Column; LiChrospher Diol 100 (250-4, Merck Inc.) (no pre-columns)
Solvent; Liquid A: hexane/2-propanol/acetic acid (82:17:1 v/v),
Liquid B: 2-propanol/water/acetic acid (85:14:1, v/v)+0.2% triethylamine
Gradient Conditions:

TABLE 1

| Time (minute) | Liquid A | Liquid B |
|---|---|---|
| 0 → 1 | 95% | 5% |
| 1 → 24 | 95 → 60% | 5 → 40% |
| 24 → 25.5 | 60% | 40% |
| 25.5 → 28 | 60 → 100% | 0% |

Flow Rate; 1.0 mL/min
Detection; ELSD evaporative light scattering detector (Shimadzu Corporation, Kyoto, Japan)

Figure 1:
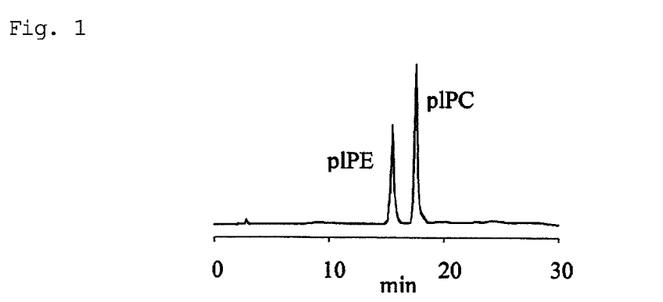
FIG. 1 shows a chromatogram obtained through analysis of a highly pure plasmalogen containing substance extracted from chicken breast meat, using HPLC-ELSD. "plPE" represents ethanolamine plasmalogens, and "plPC" represents choline plasmalogens.

The result is shown in FIG. 1. It was revealed that the plasmalogen obtained from chicken breast meat was a mixture of an ethanolamine plasmalogen (plPE) and a choline plasmalogen (plPC). When area of all detected peaks was defined as 100%, area ratio for the plasmalogens was 94.6%, wherein 47.9% was the former and 46.7% was the latter. Therefore, it was revealed that the obtained chicken breast meat derived highly pure plasmalogen containing substance contained plasmalogens by 94.6 mass %. It should be noted that a peak position of a plasmalogen can be identified by, for example, analyzing authentic samples in advance.

In the following experiment, the chicken breast meat derived highly pure plasmalogen containing substance was used as the avian-tissue extracted plasmalogen.

Example 1

Examination of Influence of Biological-Tissue Extracted Plasmalogen on Cerebral Nerve Cells The following experiment was performed for examining the influence of the avian-tissue extracted plasmalogen on cerebral nerve cells.
<Sample Preparation>

As a feed for mice used in the experiment, AIN-93M (standard feed for nutrition researches using mice and rat, published, in 1993 by the American Institute of Nutrition) was purchased (hereinafter, may be described as "ordinary feed"). In addition, through a special order, an AIN-93M containing the avian-tissue extracted plasmalogen by 0.1 mass % (hereinafter, may be described as "0.1% pl containing feed") was also purchased (both from Oriental Yeast Co., Ltd.).
<Experiment Examining Influence on Cerebral Nerve Cells>

Fourteen mice of Senescence-Accelerated Mouse-Prone 8 (SAMP8) were purchased from Japan SLC, Inc., and divided into a plasmalogen administered group (n=7) and an un-administered group (n=7). SAMP8 is a model mouse that exhibits behavioral physiological disorders including a learning/memory disorder, and reduction in immune response. The administered group was reared while being fed ad libitum with the 0.1% pl containing feed for 25 weeks. The un-administered group was reared while being fed ad libitum with ordinary feed for 25 weeks. During the rearing, water was given ad libitum. After the rearing, perfusion fixation was conducted on two mice from the administered group and two mice from the un-administered group to create cryosections in accordance with a hitherto known method, and the cryosections were immunostained and examined comparatively.

Specifically, the immunostaining was conducted as described next. A 20 μm brain section was treated in a blocking solution for 30 minutes at room temperature, and was allowed to react with an appropriately diluted primary antibody (DCX (1:500), NeuN (1:1000)) and left still overnight at 4° C. Then, the section was rinsed in PBS (phosphate buffered saline) several times, and was allowed to react with an appropriately diluted secondary antibody (1:500) and left still at room temperature for 6 hours. The section was rinsed in PBS several times to create a brain section sample. The sample was observed and analyzed using a confocal microscope. The following antibodies were used. For neuronal cell nuclei staining, the used primary antibody was an anti-neuronal nuclei antibody (anti-Neuronal Nuclei (NeuN) monoclonal antibody, derived from mice, product of Millipore Inc.), and the used secondary antibody was a fluorescent labeled anti-mouse IgG antibody (Labeled Anti-Mouse IgG antibody, Alexa Fluor 568, derived from goat, product of Molecular Probes Inc.). For staining immature neurons, the used primary antibody was a doublecortin antibody (DCX; Doublecortin (N-19): sc-8067, derived from goat, product of Santa Cruz Biotechnology Inc.), and the used secondary antibody was a fluorescent labeled anti-goat IgG antibody (Labeled Anti-Goat IgG antibody, derived from donkey, product of Molecular Probes Inc.).

It should be noted that the immunostaining method is an experimental technique that is most generally used and has the highest reliability in the current day in which researches regarding neurogenesis are actively conducted and evaluation methods and experimental technologies are improving every day. The immunostaining method is a method for visualizing an otherwise invisible antigen-antibody reaction, and is one of the techniques that are used most frequently for evaluating neurogenesis. Doublecortin (DCX), which is the molecular marker used here for neural progenitor cells, is a molecular marker used frequently for many research papers, and it can be considered as one of the molecular markers having the highest reliability. Therefore, the experimental results obtained here can also be considered to be very reliable.

Figure 2:
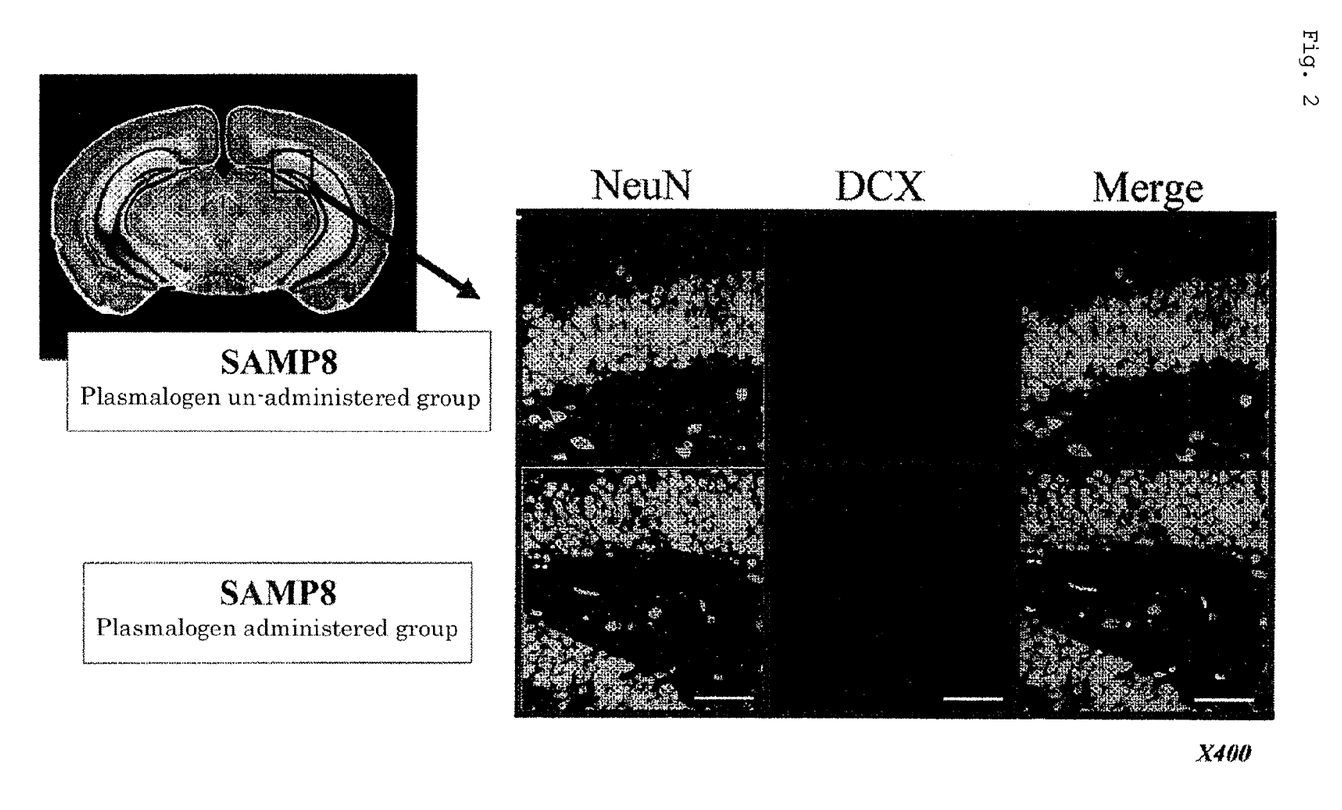
FIG. 2 shows a result of immunostaining brains of mice in a plasmalogen administered group and an un-administered group. The white scale bar presented in the image indicates 50 μm.

The result is shown in FIG. 2. FIG. 2 is an image observing the hippocampal dentate gyrus.

From the result, it was revealed that, in the hippocampal dentate gyrus, the number of cells positive for doublecortin (DCX), which is a marker for immature cerebral nerve cells, had increased in the plasmalogen administered group when compared to the plasmalogen un-administered group. These cells were also stained using an antibody against NeuN which is a marker for cerebral nerve cells, and were shown to be immature neural progenitor cells. From this, it was revealed that neogenesis of cerebral nerve cells was induced in the plasmalogen administered group.

The invention claimed is:

1. A cerebral nerve cell neogenesis method comprising a step of administering a plasmalogen to a subject at a dose effective to newly generate cerebral nerve cells, wherein not less than 90 mass % of the plasmalogen is an ethanolamine plasmalogen and a choline plasmalogen, and a mass ratio of ethanolamine plasmalogen:choline plasmalogen is 1:1.5 to 1.5:1, and wherein the subject has developed a neurological disorder in which sclerosis, atrophy, death, or reduction of cerebral nerve cells is observed.

2. The cerebral nerve cell neogenesis method according to claim 1, wherein the subject is a mammal including human.

3. The cerebral nerve cell neogenesis method according to claim 1, wherein the plasmalogen is a plasmalogen extracted from a biological tissue.

4. The cerebral nerve cell neogenesis method according to claim 3, wherein the plasmalogen is a plasmalogen extracted from an avian tissue.

5. The cerebral nerve cell neogenesis method according to claim 1, wherein the subject is a subject that has developed at least one type of neurological disorder selected from the group consisting of Alzheimer's disease, depression, schizophrenia, and dementia.

* * * * *